(12) United States Patent
Fiorina

(10) Patent No.: US 6,192,767 B1
(45) Date of Patent: Feb. 27, 2001

(54) AEROBIOLOGICAL SAMPLER FOR AIRBORNE PARTICLES

(76) Inventor: Andrea Fiorina, Regione Repalline, 103 - Campochiesa, 17031 Albenga (SV) (IT)

( * ) Notice: Subject to any disclaimer, the term of this patent is extended or adjusted under 35 U.S.C. 154(b) by 0 days.

(21) Appl. No.: 09/158,068

(22) Filed: Sep. 22, 1998

(30) Foreign Application Priority Data

Jul. 20, 1998 (IT) .............................................. MI98A1659

(51) Int. Cl.[7] .................................................... G01N 1/24
(52) U.S. Cl. ................................ 73/863.21; 73/864.34; 73/864.71
(58) Field of Search ........................... 73/864.71, 863.03, 73/863.21, 863.23, 863.25, 864.34

(56) References Cited

U.S. PATENT DOCUMENTS

| | | | |
|---|---|---|---|
| 3,572,128 | * 3/1971 | Hemeon | 73/864.71 X |
| 4,075,389 | * 2/1978 | Vassiliades et al. | 428/306 |
| 4,277,259 | * 7/1981 | Rounbehler et al. | 73/863.21 X |
| 4,961,916 | * 10/1990 | Lesage et al. | 73/863.21 X |
| 5,243,864 | * 9/1993 | Dunmyre et al. | 73/864.71 |
| 5,319,986 | * 6/1994 | Padden et al. | 73/863.21 |
| 5,438,885 | * 8/1995 | Zelazny | 73/864.71 |
| 5,517,866 | * 5/1996 | Manning et al. | 73/863.21 |
| 5,607,497 | * 3/1997 | Brown | 73/864.71 |
| 5,691,195 | * 11/1997 | Doleans et al. | 73/864.71 X |
| 5,693,895 | * 12/1997 | Baxter | 73/864.71 X |

FOREIGN PATENT DOCUMENTS

| | | | |
|---|---|---|---|
| 145037 | * 11/1980 | (DE) | 73/863.21 |
| 147303 | * 7/1985 | (EP) | 73/864.34 |
| 2048468A | * 12/1980 | (GB) | 73/863.21 |
| 2158233A | * 11/1985 | (GB) | 73/864.34 |
| 60-129644 | * 7/1985 | (JP) | 356/36 |
| 61-71346 | * 4/1986 | (JP) | 435/182 |
| 63-75639 | * 4/1988 | (JP) | 73/863.21 |

OTHER PUBLICATIONS

*Allergy 1997*; 52:1026–1030, Copyright By Munksgaard (published Oct. 1997). Author A. Fiorina et al "Aerobiologic Particle Sampling By a New Personal Collector (Partrap FA52) in comparison to the Hirst (Burkard) Sampler".

Abstract of JP 79043920 B By Derwent Information LTD Entitled "Colorimetric Determination of Bio–Polymers Esp. Serum Protein—By Spreading Samples Electrophoretically on Cellulose Acetate Tape, Making Tape Transparent and Scanning with Light Beam", Dec. 1979.*

* cited by examiner

*Primary Examiner*—Thomas P. Noland
(74) *Attorney, Agent, or Firm*—Armstrong, Westerman, Hattori, McLeland & Naughton

(57) ABSTRACT

A portable sampler able to collect airborne particles present in the surrounding air with characteristics of sampling air at particular aspiration flow corresponding to a medium value of current volume of air (ten liters per minute) that is mobilized by an adult subject during quiet respiration at rest, directly at 10–20 cm from mouth and nose of the examined person. This instrument equipped with a particular model of disposable sampling chamber permits valuation of pollen grains, allergens, mycetes, bacteria, viruses, organic and inorganic particles with different possibilities of use in allergology, hygiene, work medicine, and legal medicine.

7 Claims, 1 Drawing Sheet

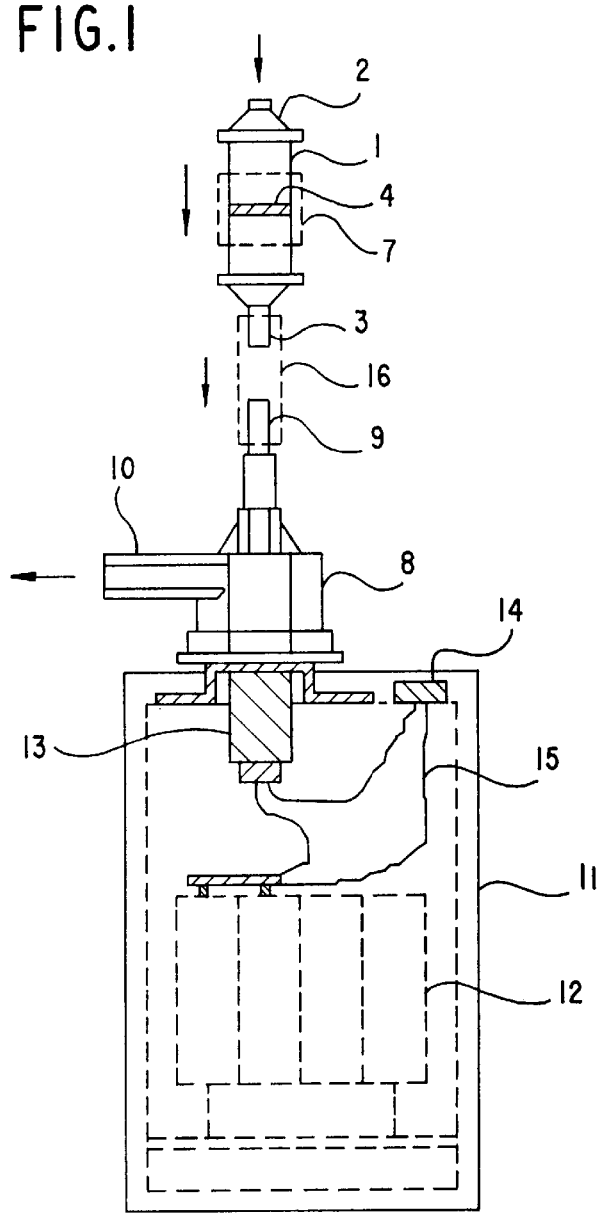
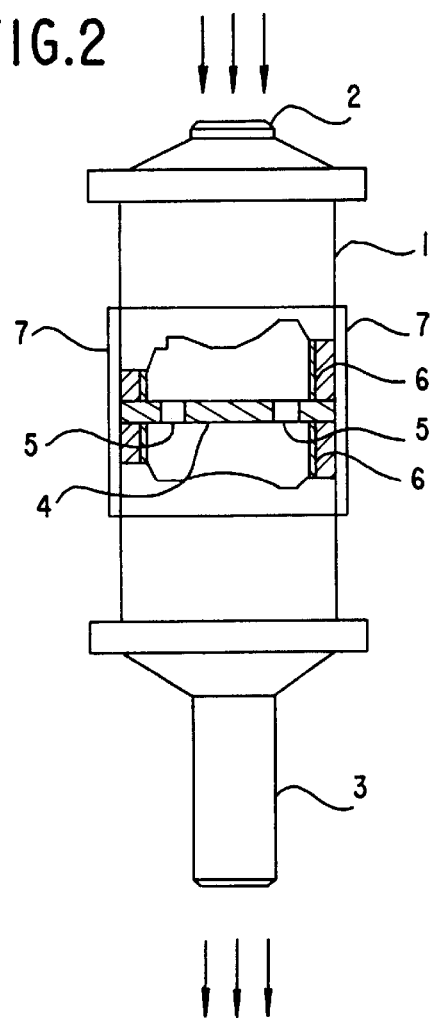
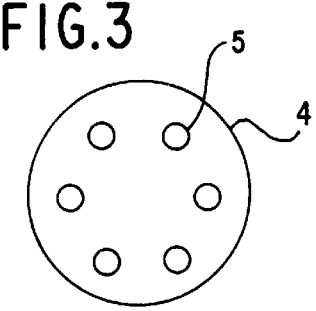

AEROBIOLOGICAL SAMPLER FOR AIRBORNE PARTICLES

The object of the present invention consists in a sampler instrument able to collect airborne particles of various dimensions, even very little, that are dispersed in the atmosphere.

In particular this sampler is able to collect particles both of inorganic nature, as dusts, and of organic nature, as viruses, bacteria, spores, mycetes, pollen grains and so on. In case of personal utilisation, i.e. when it is necessary to determine a particular parameter relative to the physical condition of a person in relation to the surrounding atmosphere, this instrument is able to sample and monitor the atmospheric condition directly near the person, particularly near his or her mouth, using the same medium flows of respiration of an adult subject at rest, corresponding to the aspiration medium flow of about 10 liters per minute.

Many instruments able to sample airborne particles are know in the art: these instruments fixed or movable, are of greater dimensions when considered in comparison with the described instrument, or, if of the same dimensions, they are not so exact in the quantitative determination of substances present in the atmosphere and certainly they are not able to monitor the atmospheric air conditions at a medium aspiration value corresponding to the air flow mobilised during a quiet respiration of an adult at rest and in a healthy condition.

The sampling instrument, object of this invention is of pocket size, of negligible weight, can be utilised for a long period and does not interfere with the normal life of the person who utilises it. Due to these peculiarities, it does not present difficulties when used by old people and children.

This instrument can be utilised for sampling airborne particles by a survey that can have hourly or daily programmes, or during a work shift in varied conditions; this instrument can be worn by a person or can be installed in a fixed position in a strategic point or in a mobile position, on a revolving tripod with a wing which will permit it to sample against the wind force. The sampling instrument object of the present invention can be utilised in studies of different types such as studies of aerobiology, allergology, immunology, bacteriology and virology, allowing the taking-in of particles present in the atmosphere where a determined person lives, works or rests. Therefore, it is possible to do a timed and targeted atmosphere sampling that can find and quantify airborne particles in the aspirated air and also to evaluate the possible ratio of cause and effect between pathogen agent and the pathology of the patient affected by the disease, for example rhinitis, bronchial asthma, allergic alveolitis, pneumoconiosis, infections of the broncopulmonary apparatus.

It is very useful to correlate the data of air sampling with a very detailed record of symptoms evidenced by the patient examined, with a description of his daily activity and with the characteristics of his surroundings during the sampling time.

Therefore, we can have manifold uses of the object of the invention:

in the diagnosis of ORL, oculistic, respiratory, dermatologic (with allergic pathogeny) diseases;

for virological, bacteriological, mycological studies of pure research or in practical hygienistic employments, such as, the study of hospital infections, the study of ambience regarding the sterility characteristics of operating theatres, of transplant centers, and the study of industrial centers, e.g. the monitoring of sterility of the ambience used for manipulation and packaging of drugs and foods;

in the field of work medicine for environmental monitoring and for the diagnosis of professional diseases;

in botany for scientific, morphologic and genetic studies;

agriculture for studying the vital cycle of parasites and, consequently, for a beneficial and correct use of pesticides;

in legal medicine for identification of particles found on the scene of the crime;

for the safeguarding of cultural and artistic works of art, e.g. in picture galleries, libraries, for the identification of parasites that can irremediably damage works of art.

The instrument of the present invention is compact, light in weight and easy to transport; it allows the performance of sampling also during the movements of the person, as well as an accurate evaluation of the nature and quantity of the airborne particles in the atmosphere with which the person is in contact at a determined time.

Furthermore this instrument can be produced at a very competitive price, it is portable and simple to use and, therefore, represents an advance in respect to similar instruments on the market at present.

SUMMARY OF THE INVENTION

The sampling instrument for airborne particles, object of the present invention, essentially consists of three elements: a disposable sampling chamber, an aspirative turbine and a case containing the batteries and the electric circuit for driving the turbine.

The sampling chamber is disposable and, dependent on the type of airborne particles researched, presents different characteristics, suitable to their sampling which can be of aerobiologic, bacteriologic, sporologic, virologic and environmental type with organic and inorganic particles. This chamber is essentially made of a cylindric body subdivided with an apposite perforated diaphragm and is furnished of an inlet cone aspirator and outlet cone of exit for the air.

Inside this chamber is located a cellulose acetate tape that, as it is flexible, assumes the form of the internal lateral surface of the cylindric chamber. The cellulose acetate tape is opportunely coated with a particular substance that is adhesive and so does not permit the particles drawn on its surface to go away: preferentially used is, in aerobiological sampling, silicone oil.

The sampling chamber is divided in two cylindrical parts, each part having in the inside the cellulose acetate tape opportunely treated, these parts are arranged in a coaxial way one in respect to the other, making an appropriate matching connection and having interposed, on the junction surface, a diaphragm which has an appropriate number of holes, preferably from 3 to 9, and, more preferably, 6, that provoke a whirly air flow, homogeneous and facilitate the deposition of the airborne particles on the cellulose acetate tape.

In the case of virologic, bacteriologic and mycologic sampling, the sampling chamber can contain, alternatively to the cellulose acetate tape, a Petri capsule inserted inside at an opportune distance from the perforated diaphragm.

Eventually, the holes present on the diaphragm are made on the frustum of the cone, this fact determines an impact of air flow directly on the surface of culture medium, facilitating in this way the deposition of particles inside the Petri capsule.

In alternative to this realisation, instead of the Petri capsule, a particular membrane of the millipore type of cyrolite can be utilised, which permits to capture the viruses, bacteria and microscopic fungi inside and, subsequently, cultivate them sterilely in a culture medium on a Petri capsule containing a selected culture medium.

The second element of the instrument, the aspirative turbine, has well defined characteristics consisting essentially in offering constant aspiration flow in time, generally fixed in ten liters per minute, this value is taken as a physiologic parameter of reference because it represents current respiratory volume, but is eventually modifiable according to the need of research or of study.

The third element of the instrument is a case containing the engine, the electric circuit and the rechargeable batteries that furnish electric energy at low voltage for driving turbine: this case is furnished, on the outside, with a push button for operating the turbine. For a better comprehension of the sampling instrument, reference is made to the enclosed designs in which is represented a preferred realisation of the invention: these designs are not, however, limitative of the same invention.

BRIEF DESCRIPTION OF THE DRAWINGS

FIG. 1 represents a frontal view of sampling instrument assembled in its three elements which evidence the internal part, referred to the third element containing the engine, the batteries and the electric circuit;

FIG. 2 represents a frontal view of the sampling chamber and a partial section of the same according to a plan passing through its longitudinal axis;

FIG. 3 represents a plan view of the separating diaphragm of the sampling chamber.

DETAILED DESCRIPTION OF THE PREFERRED EMBODIMENTS

In these figures are pointed out the first element or sampling chamber 1 furnished of the inlet nozzle 2, the outlet cone 3 and the diaphragm 4 on which are present the holes 5 in number of six; the cellulose acetate tape 6 is made adhesive with silicone oil, this adhesive tape, divided between the two parts of the sampling chamber 1, at the top and bottom of the diaphragm 4; the element of junction 7, constituted by adhesive flexible tape; the second element 8 in which is inserted an aspirate turbine not represented in the design, furnished of inlet nozzle 9 and of outlet 10 of the air; the third element 11 containing the batteries 12, the engine 13, the push button 14, and the electric circuit 15 that connects these parts. This third element 11 can be eventually the instrument's handle.

The connection between sampling chamber 1 and the second element 8 is assisted by a tube 16, represented by the dotted line in FIG. 1, that can be rigid or flexible on condition that it cannot be compressible; this tube is connected respectively with the sampling chamber and with the turbine through gate 3 and 9.

At the moment of use, for making the sampling of airborne particles in a determined place, the aspirative turbine, dimensioned for determining a constant aspiration flow in time and, preferably, of 10 liters per minute, is actioned by push button 14; the aspirated air, the transit of which is indicated in the designs by arrows, goes in the sampling chamber 1 through the nozzle 2 and the aerobiological particles contained inside remain attached, by a quantitatively more elevated efficiency, on the adhesive tape 6. The high efficiency of adhesion of the particles is assured by the turbulence in the chamber due to the presence of diaphragm opportunely perforated.

The aspirated air goes out from sampling chamber 1 through the gate 3 and through the connection tube 16 and the gate 9 passes through the aspirative turbine that send it to the atmosphere through the gate 10. At the programmed time the turbine is stopped, using the push button 14 located on the third element 11 of sampling instrument, the sampling chamber 1 is removed from instrument and, closed in a sterile case, as for example a plastic case for culture, and is sent to a laboratory for analysis.

The insertion of a new sampling chamber in the sampling instrument renders it immediately usable for a new sampling.

The disposable sampling chamber of sampling instrument is made of suitable plastic, preferably transparent.

What is claimed is:

1. Portable personal sampling instrument for sampling airborne particles comprising a sampling chamber, aspirative turbine and a case containing an engine, an electric circuit and rechargeable batteries, the turbine being connected to the sampling chamber and the case, wherein the sampling chamber, having an inlet nozzle and an outlet gate, is disposable and includes a cylindrical body divided in two cylindrical parts, each part having inside, on a wall, a flexible cellulose acetate tape, made adhesive with a substance, these parts of the cylindrical body being disposed in a coaxial way with respect to each other, making a matching connection and having, interposed on their junction surface, a diaphragm perforated with a number of holes from 3 to 9, and wherein the turbine, having an inlet nozzle and an outlet gate, provides an aspiration flow of air which is constant in time.

2. Portable personal sampling instrument according to claim 1, wherein the flexible cellulose acetate tape is treated by silicone oil.

3. Portable personal sampling instrument according to claim 2, wherein the diaphragm has 6 holes.

4. Portable personal sampling instrument according to claim 3, wherein the turbine provides a constant aspiration air flow of 10 liters per minute.

5. Portable personal sampling instrument according to claim 1, wherein the diaphragm has 6 holes.

6. Portable personal sampling instrument according to claim 5, wherein the turbine provides a constant aspiration air flow of 10 liters per minute.

7. Portable personal sampling instrument according to claim 1, wherein the turbine provides a constant aspiration air flow of 10 liters per minute.

* * * * *